(12) United States Patent
Yokoyama

(10) Patent No.: US 7,307,096 B2
(45) Date of Patent: Dec. 11, 2007

(54) COMBINED AGENTS FOR TREATMENT OF GLAUCOMA

(75) Inventor: Tomihisa Yokoyama, Saitama (JP)

(73) Assignee: Sankyo Company, Limited, Tokyo (JP)

( * ) Notice: Subject to any disclaimer, the term of this patent is extended or adjusted under 35 U.S.C. 154(b) by 732 days.

(21) Appl. No.: 10/146,747

(22) Filed: May 16, 2002

(65) Prior Publication Data

US 2003/0040529 A1 Feb. 27, 2003

Related U.S. Application Data

(63) Continuation-in-part of application No. PCT/JP00/08545, filed on Dec. 1, 2000.

(30) Foreign Application Priority Data

Dec. 1, 1999 (JP) .................................. 11-341524
Mar. 21, 2000 (JP) ............................. 2000-078769

(51) Int. Cl.
*A61K 31/41* (2006.01)
(52) U.S. Cl. ........................ 514/382; 514/913; 514/922
(58) Field of Classification Search ................. 514/180, 514/236.5, 227.8, 235.8, 303, 340, 381, 395, 514/397, 530, 912, 913
See application file for complete search history.

(56) References Cited

U.S. PATENT DOCUMENTS

| | | | |
|---|---|---|---|
| 5,175,161 A * | 12/1992 | Yokoyama et al. | 514/236.5 |
| 5,182,264 A | 1/1993 | Watkins | |
| 5,250,521 A | 10/1993 | Allen et al. | |
| 5,273,976 A * | 12/1993 | Yokoyama et al. | 514/242 |
| 5,925,664 A | 7/1999 | Yokoyama et al. | |
| 6,777,436 B2 * | 8/2004 | Yokoyama et al. | 514/381 |

FOREIGN PATENT DOCUMENTS

| | | |
|---|---|---|
| CA | 2 247 208 A | 9/1997 |
| CA | 2 293 325 A1 | 11/1998 |
| CN | 1075634 A | 9/1993 |
| EP | 42299 B1 | 9/1984 |
| EP | 189 690 A1 | 8/1986 |
| EP | 0 296 879 B1 | 12/1988 |
| EP | 0 375 299 A1 | 6/1990 |
| EP | 490587 A1 | 6/1992 |
| EP | 0 628 313 A1 | 12/1994 |
| EP | 631780 A1 | 1/1995 |
| EP | 639 563 A2 | 2/1995 |
| EP | 795 326 B1 | 9/1997 |
| GB | 1253710 | 11/1971 |
| GB | 1398455 | 6/1975 |
| JP | 64-026518 | 1/1989 |
| JP | 64-26518 A | 1/1989 |
| WO | WO 90/02533 A2 | 3/1990 |
| WO | WO 90/02553 A1 | 3/1990 |
| WO | 91/15206 A1 | 10/1991 |
| WO | WO 92/20342 A1 | 11/1992 |
| WO | 93/16701 A2 | 9/1993 |
| WO | 95/21609 A1 | 8/1995 |
| WO | 95/24902 A1 | 9/1995 |
| WO | WO 97/37688 A2 | 10/1997 |
| WO | 98/41208 A1 | 9/1998 |

OTHER PUBLICATIONS

H.J. Kaiser, T. Graf, G. Krejci, G.A. Mathis, A Jauch and J. Flammer, "A New Angiotensin-II-Receptor Blocker, CGP 48933 : Local Tolerance and Effect on Intraocular Pressure. A Pilot Study", *European Journal of Ophthalmology*, 1, 1997, 35-39.

Z. S. Popova, T. N. Terkhina, "Our Experience of Applying Prostaglandin F2 Alpha Analogue—Latanoprost (Xalatan) for Treating Glaucoma", *Kremlevskaya Medicinia, Klinichesky Vestnik*, No. 4, (Oct.-Dec. 2000), pp. 78-79.

Z.S. Popova, T.N. Terekhina, "Trial of using latanoprost (xalathane), the analogue of prostaglandin F2-alpha, in glaucoma therapy," *Kreml. Med.: Clin Vestn.*, 2000, No. 4, pp. 78-79.

Hejkal TW et al., *Semin Ophthalmol.*, 1999, 14(3), pp. 114-123.

Camras CB et al., *Am. J. Ophthalmol.*, 1998, 126(3), pp. 390-391.

Camras CB, Alm A, Watson P, Stjernschantz J., Group USLS. Fechtner RD, "Latanoprost, a prostaglandin analog, for glaucoma therapy. Efficacy and safety after one year of treatment in 198 patients," *Ophthalmology*, 1996, 103(11), 1916-1924.

* cited by examiner

*Primary Examiner*—Frederick Krass
(74) *Attorney, Agent, or Firm*—Frishauf, Holtz, Goodman & Chick, P.C.

(57) ABSTRACT

A pharmaceutical composition for the prophylaxis or treatment of glaucoma which comprises an angiotensin II antagonist and at least one compound selected from an adrenaline receptor blocker, a prostaglandin and a carbonic anhydrase inhibitor; and a method for the prophylaxis or treatment of glaucoma by administering the composition to a patient.

4 Claims, No Drawings

COMBINED AGENTS FOR TREATMENT OF GLAUCOMA

CROSS REFERENCE TO RELATED APPLICATION

This application is a continuation-in-part application of International Application No. PCT/JP00/08545 filed Dec. 1, 2000.

FIELD OF THE INVENTION

The present invention relates to a prophylactic or therapeutic agent (pharmaceutical composition) for glaucoma having excellent intraocular pressure lowering action and a method for preventing or treating glaucoma by administering the composition to a patient.

BACKGROUND OF THE INVENTION

β-Blockers (timolol maleate, carteolol, etc.), prostaglandin type compounds (isopropyl unoprostone and latanoprost) and a carbonic anhydrase inhibitor (dorzolamide hydrochloride) have been mainly used as agents for the treatment of glaucoma. Moreover, an α1-blocker (bunazosin hydrochloride) and an αβ-blocker (nipradilol) are now at the stage of clinical trials or application for approval.

There are reports (for example, EP795326, EP631780, WO95/21609, WO91/15206, etc.) that angiotensin II antagonists are useful agents for the treatment of glaucoma. Among angiotensin II antagonists, only CGP-48933 has been subjected to clinical trial. It was reported that its effect for glaucoma was insufficient (Eur. J. Ophthalmol. 1997, January-March; 7(1): 35-9) and the development of it has been stopped since then.

SUMMARY OF THE INVENTION

The present inventors have carried out an extensive investigation on the preparation of agents for the prophylaxis or treatment of glaucoma having superior intraocular pressure lowering effect and on their pharmacological action. As a result, it has been found that an intraocular pressure lowering action can be potentiated by using an angiotensin II antagonist in combination with at least one compound selected from adrenaline receptor blockers, prostaglandins and carbonic anhydrase inhibitors, leading to the completion of the present invention.

The present invention relates to the following:
(1) an agent for the prophylaxis or treatment of glaucoma, which comprises an angiotensin II antagonist and at least one compound selected from adrenaline receptor blockers, prostaglandins and carbonic anhydrase inhibitors as active ingredients for simultaneous, separate or successive use of these active ingredients.

Of these agents, especially preferred are the following:
(2) an agent for the prophylaxis or treatment of glaucoma, wherein the angiotensin II antagonist is a compound having the below-described formula (I) or a pharmacologically acceptable salt, ester or other derivative thereof:

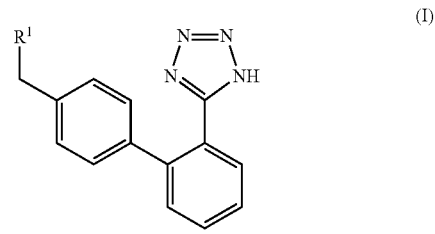

wherein, $R^1$ represents a group having the below-described structural formula (Ia), (Ib), (Ic), (Id), (Ie) or (If):

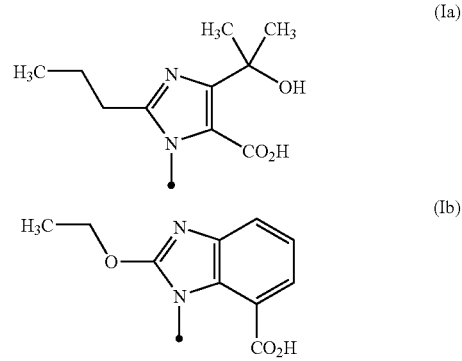

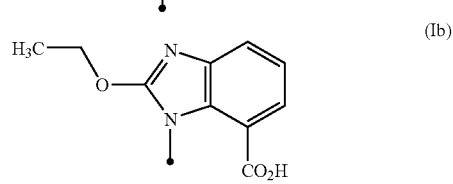

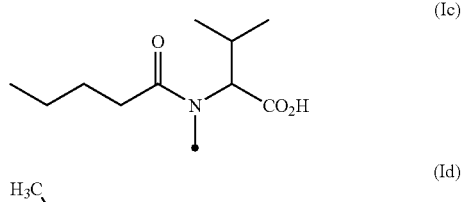

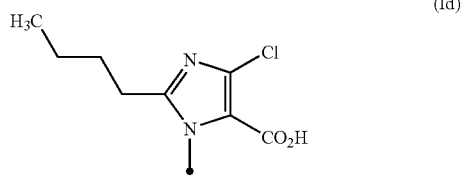

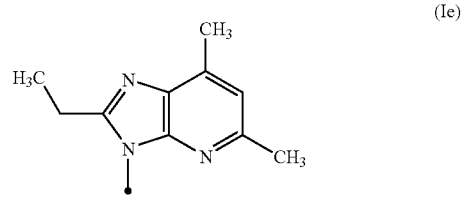

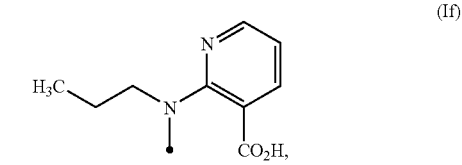

(3) an agent for the prophylaxis or treatment of glaucoma as described in (2), wherein $R^1$ represents a group having the formula (Ia), (Ib) or (Ic), (4) an agent for the prophylaxis or treatment of glaucoma as described in (2), wherein $R^1$ represents a group having the formula (Ia), (5) an agent for the prophylaxis or treatment of glaucoma, wherein the adrenaline receptor blocker is bunazosin, timolol or nipradilol, or a pharmacologically acceptable salt or ester thereof, (6) an agent for the prophylaxis or treatment of glaucoma, wherein the adrenaline receptor blocker is bunazosin hydrochloride, timolol maleate or nipradilol, (7) an agent for the prophylaxis or treatment of glaucoma, which comprises an angiotensin II antagonist and at least one compound selected from prostaglandins and carbonic anhydrase inhibitors as active ingredients for simultaneous, separate or successive use thereof, (8) an agent for the prophylaxis or treatment of glaucoma, wherein the prostaglandin is isopropyl unoprostone or latanoprost, or a pharmacologically acceptable salt thereof, (9) an agent for the prophylaxis or treatment of glaucoma, wherein the prostaglandin is isopropyl unoprostone or latanoprost,

(10) an agent for the prophylaxis or treatment of glaucoma, wherein the carbonic anhydrase inhibitor is dorzolamide or a pharmacologically acceptable salt thereof,

(11) an agent for the prophylaxis or treatment of glaucoma, wherein the carbonic anhydrase inhibitor is dorzolamide hydrochloride, and

(12) an agent for the prophylaxis or treatment of glaucoma as described in any one selected from (1) to (11) above, which is in a form suitable for topical application to the eyes.

The present invention also relates to:

(13) a method for preventing or treating glaucoma, which comprises administering an agent for the prophylaxis or treatment of glaucoma as described in any one selected from (1) to (11) above.

DETAILED DESCRIPTION OF THE INVENTION

In the present invention, the term "angiotensin II antagonist" means a compound which exhibits antagonism against angiotensin II in an angiotensin II receptor, thereby weakening the action of angiotensin II. Compounds capable of inhibiting over 50% of the function of angiotensin II at a concentration of 1 µM are preferred, of which angiotensin II selective antagonists are more preferred. Especially preferred as "angiotensin II antagonists" are the compounds of the following formula (I) or pharmacologically acceptable salts thereof, or esters thereof or other derivatives thereof:

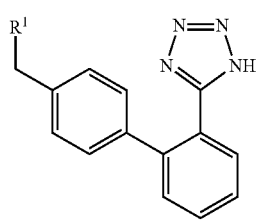

(I)

wherein $R^1$ represents the following structural formula (Ia), (Ib), (Ic), (Id), (Ie) or (If):

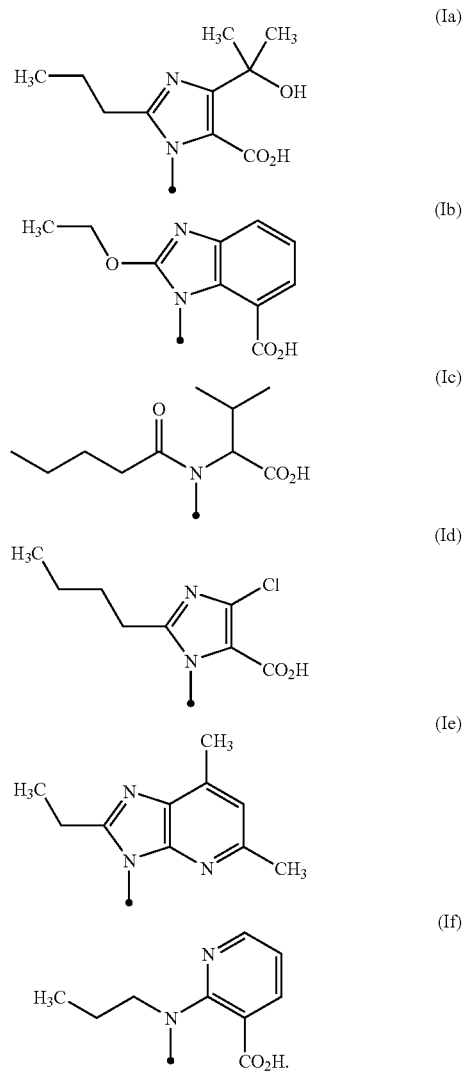

Of the above-described compounds of formula (I), preferred are the compounds having a group of formula (Ia), (Ib) or (Ic) as $R^1$, of which the compounds having a group of formula (Ia) as $R^1$ are especially preferred.

The term "adrenaline receptor blocker" as used herein means one of α-blockers, β-blockers and αβ-blockers. Preferred as the α-blocker are α1-blockers, of which bunazosin or a pharmacologically acceptable salt thereof is especially preferred, with bunazosin hydrochloride being most preferred. Especially preferred as the β-blocker is timolol or a pharmacologically acceptable salt thereof or an ester thereof, of which timolol maleate is most preferred. Especially preferred as the αβ-blocker is nipradilol or a pharmacologically acceptable salt thereof or an ester thereof, of which nipradilol is most preferred.

The term "prostaglandin" means any one of naturally existing prostaglandins such as prostaglandin F2α or prostaglandin derivatives such as isopropyl unoprostone and latanoprost, or a pharmacologically acceptable salt thereof.

Of these, isopropyl unoprostone or latanoprost, or a pharmacologically acceptable salt thereof is especially preferred, of which isopropyl unoprostone or latanoprost is most preferred.

As the "carbonic anhydrase inhibitor", dorzolamide or a pharmacologically acceptable salt thereof is especially preferred, of which dorzolamide hydrochloride is most preferred.

The term "pharmacologically acceptable salt" means a salt, which can be formed when the "angiotensin II antagonist", "adrenaline receptor blocker", "prostaglandin" and/or "carbonic anhydrase inhibitor" has an acidic group such as carboxyl or a basic group such as amino or imino.

Preferred examples of the salt formed with an acidic group include alkali metal salts such as a sodium salt, potassium salt or lithium salt, alkaline earth metal salts such as a calcium salt or magnesium salt, metal salts such as an aluminum salt or iron salt; amine salts, e.g., inorganic salts such as an ammonium salt and organic salts such as a t-octylamine salt, dibenzylamine salt, morpholine salt, glucosamine salt, phenylglycine alkyl ester salt, ethylenediamine salt, N-methylglucamine salt, guanidine salt, diethylamine salt, triethylamine salt, dicyclohexylamine salt, N,N'-dibenzylethylenediamine salt, chloroprocaine salt, procaine salt, diethanolamine salt, N-benzylphenethylamine salt, piperazine salt, tetramethylammonium salt or tris(hydroxymethyl)aminomethane salt; and amino acid salts such as a glycine salt, lysine salt, arginine salt, ornithine salt, glutamate or aspartate.

Preferred examples of the salt formed with a basic group include hydro-halides such as a hydrofluoride, hydrochloride, hydrobromide or hydroiodide, inorganic acid salts such as a nitrate, perchlorate, sulfate or phosphate; lower alkanesulfonates such as a methanesulfonate, trifluoromethanesulfonate or ethanesulfonate, arylsulfonates such as a benzenesulfonate or p-toluenesulfonate, organic acid salts such as an acetate, malate, fumarate, succinate, citrate, ascorbate, tartrate, oxalate or maleate; and amino acid salts such as a glycine salt, lysine salt, arginine salt, ornithine salt, glutamate or aspartate.

When a "pharmacologically acceptable salt" is allowed to stand in the atmosphere or is recrystallized, it sometimes absorbs water to form a hydrate.

Such a hydrate is also embraced in the present invention.

The term "ester or other derivative" means a compound which is produced by modifying a functional group (e.g. hydroxyl, carboxyl, amino or the like group) of the "angiotensin II antagonist" with a protecting group in a manner known per se in the art, and is a derivative converted into an "angiotensin II antagonist" by administration to the living body. By administering the compound intravenously, orally or in eye drops to experimental animals such as rats or mice, examining their body fluids and confirming the angiotensin II antagonism of the compound thus detected, the compound can be determined whether it is such a derivative or not.

Examples of the "ester" include "esters formed with a hydroxyl group" and "esters formed with a carboxyl group". The term "ester" means an ester whose ester residue is a "conventional protecting group" or a "protecting group removable in vivo by a biological method such as hydrolysis".

The term "conventional protecting group" means a protecting group removable by a chemical method such as hydrogenolysis, hydrolysis, electrolysis or photolysis.

Preferred examples of the "conventional protecting group" related to the "ester formed with a hydroxyl group" include "aliphatic acyl groups" (preferably, lower aliphatic $C_{1-6}$ acyl groups), for example, alkanoyl groups such as a formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, eicosanoyl or heneicosanoyl group, halogeno-alkylcarbonyl groups such as a chloroacetyl, dichloroacetyl, trichloroacetyl or trifluoroacetyl group, lower alkoxyalkylcarbonyl groups such as a methoxyacetyl group, and unsaturated alkylcarbonyl groups such as an acryloyl, propioloyl, methacryloyl, crotonoyl, isocrotonoyl or (E)-2-methyl-2-butenoyl group; "aromatic acyl groups", for example, arylcarbonyl groups such as a benzoyl, α-naphthoyl or β-naphthoyl group, halogeno-arylcarbonyl groups such as a 2-bromobenzoyl or 4-chlorobenzoyl group, lower alkylated arylcarbonyl groups such as a 2,4,6-trimethylbenzoyl or 4-toluoyl group, lower alkoxylated arylcarbonyl groups such as a 4-anisoyl group, nitrated arylcarbonyl groups such as a 4-nitrobenzoyl or 2-nitrobenzoyl group, lower alkoxycarbonylated arylcarbonyl groups such as a 2-(methoxycarbonyl)benzoyl group, and arylated arylcarbonyl groups such as a 4-phenylbenzoyl group; "alkoxycarbonyl groups", for example, lower alkoxycarbonyl groups such as a methoxycarbonyl, ethoxycarbonyl, propoxycarbonyl, butoxycarbonyl, s-butoxycarbonyl, t-butoxycarbonyl or isobutoxycarbonyl group, and lower alkoxycarbonyl groups substituted with a halogen or tri(lower alkyl)silyl group such as a 2,2,2-trichloroethoxycarbonyl or 2-trimethylsilylethoxycarbonyl group; "tetrahydropyranyl or tetrahydrothiopyranyl groups" such as a tetrahydropyran-2-yl, 3-bromotetrahydropyran-2-yl, 4-methoxytetrahydropyran-4-yl, tetrahydrothiopyran-2-yl or 4-methoxytetrahydrothiopyran-4-yl group; "tetrahydrofuranyl or tetrahydrothiofuranyl groups" such as a tetrahydrofuran-2-yl or tetrahydrothiofuran-2-yl group; "silyl groups", for example, tri(lower alkyl)silyl groups such as a trimethylsilyl, triethylsilyl, isopropyldimethylsilyl, t-butyldimethylsilyl, methyldiisopropylsilyl, methyldi-t-butylsilyl or triisopropylsilyl group, and tri(lower alkyl)silyl groups substituted with one or two aryl groups such as a diphenylmethylsilyl, diphenylbutylsilyl, diphenylisopropylsilyl or phenyldiisopropylsilyl group; "alkoxymethyl groups", for example, lower alkoxymethyl groups such as a methoxymethyl, 1,1-dimethyl-1-methoxymethyl, ethoxymethyl, propoxymethyl, isopropoxymethyl, butoxymethyl or t-butoxymethyl group, lower alkoxylated (lower alkoxy)methyl groups such as a 2-methoxyethoxymethyl group and halogeno(lower alkoxy)methyl groups such as a 2,2,2-trichloroethoxymethyl or bis(2-chloroethoxy)methyl group; "substituted ethyl groups", for example, lower alkoxylated ethyl groups such as a 1-ethoxyethyl or 1-(isopropoxy)ethyl group and halogenated ethyl groups such as a 2,2,2-trichloroethyl group; "aralkyl groups", for example, lower alkyl groups substituted with 1 to 3 aryl groups such as a benzyl, α-naphthylmethyl, β-naphthylmethyl, diphenylmethyl, triphenylmethyl, α-naphthyldiphenylmethyl or 9-anthrylmethyl group and lower alkyl groups substituted with 1 to 3 aryl groups having an aryl ring substituted with a lower alkyl, lower alkoxy, nitro, halogen or cyano group such as a 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl or 4-cyanobenzyl group; "alkenyloxycarbonyl groups" such as a vinyloxycarbonyl or allyloxycarbonyl group; and "aralkyloxycarbonyl groups" which may have an aryl ring substituted by 1 or 2 lower alkoxy or nitro groups such as a benzyloxycarbonyl, 4-methoxybenzyloxycarbonyl, 3,4-dimethoxybenzyloxycarbonyl, 2-nitrobenzyloxycarbonyl or 4-nitrobenzyloxycarbonyl group.

Preferred examples of the "conventional protecting group" related to the "ester formed with a carboxyl group" include lower alkyl groups such as a methyl, ethyl, n-propyl, isopropyl, n-butyl, isobutyl, s-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl or 2-ethylbutyl group; lower alkenyl groups such as an ethenyl, 1-propenyl, 2-propenyl, 1-methyl-2-propenyl, 1-methyl-1-propenyl, 2-methyl-1-propenyl, 2-methyl-2-propenyl, 2-ethyl-2-propenyl, 1-butenyl, 2-butenyl, 1-methyl-2-butenyl, 1-methyl-1-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 1-hexenyl, 2-hexenyl, 3-hexenyl, 4-hexenyl or 5-hexenyl group; lower alkynyl groups such as an ethynyl, 2-propynyl, 1-methyl-2-propynyl, 2-methyl-2-propynyl, 2-ethyl-2-propynyl, 2-butynyl, 1-methyl-2-butynyl, 2-methyl-2-butynyl, 1-ethyl-2-butynyl, 3-butynyl, 1-methyl-3-butynyl, 2-methyl-3-butynyl, 1-ethyl-3-butynyl, 2-pentynyl, 1-methyl-2-pentynyl, 2-methyl-2-pentynyl, 3-pentynyl, 1-methyl-3-pentynyl, 2-methyl-3-pentynyl, 4-pentynyl, 1-methyl-4-pentynyl, 2-methyl-4-pentynyl, 2-hexynyl, 3-hexynyl, 4-hexynyl or 5-hexynyl group; halogeno(lower alkyl) groups such as a trifluoromethyl, trichloromethyl, difluoromethyl, dichloromethyl, dibromomethyl, fluoromethyl, 2,2,2-trifluoroethyl, 2,2,2-trichloroethyl, 2-bromoethyl, 2-chloroethyl, 2-fluoroethyl, 2-iodoethyl, 3-chloropropyl, 4-fluorobutyl, 6-iodohexyl or 2,2-dibromoethyl group; hydroxy("lower alkyl groups") such as a 2-hydroxyethyl, 2,3-dihydroxypropyl, 3-hydroxypropyl, 3,4-dihydroxybutyl or 4-hydroxybutyl group; "lower aliphatic acyl"-"lower alkyl groups" such as an acetylmethyl group; the above-exemplified "aralkyl groups"; and the above-exemplified "silyl groups".

The term "protecting group removable in vivo by a biological method such as hydrolysis" means a protecting group removable in vivo by a biological method such as hydrolysis to produce a free acid or its salt. In order to determine whether a compound is such a derivative or not, one can administer the compound by intravenous injection to experimental animals such as rats or mice, followed by examination of their body fluids to confirm the angiotensin II antagonism of the compound thus detected.

Preferred examples of the "protecting group removable in vivo by a biological method such as hydrolysis" related to the "ester formed with a hydroxyl group" include "carbonyloxyalkyl groups" which are 1-(acyloxy)-"lower alkyl groups", for example, 1-("lower aliphatic acyl"oxy)-"lower alkyl groups" such as a formyloxymethyl, acetoxymethyl, dimethylaminoacetoxymethyl, propionyloxymethyl, butyryloxymethyl, pivaloyloxymethyl, valeryloxymethyl, isovaleryloxymethyl, hexanoyloxymethyl, 1-formyloxyethyl, 1-acetoxyethyl, 1-propionyloxyethyl, 1-butyryloxyethyl, 1-pivaloyloxyethyl, 1-valeryloxyethyl, 1-isovaleryloxyethyl, 1-hexanoyloxyethyl, 1-formyloxypropyl, 1-acetoxypropyl, 1-propionyloxypropyl, 1-butyryloxypropyl, 1-pivaloyloxypropyl, 1-valeryloxypropyl, 1-isovaleryloxypropyl, 1-hexanoyloxypropyl, 1-acetoxybutyl, 1-propionyloxybutyl, 1-butyryloxybutyl, 1-pivaloyloxybutyl, 1-acetoxypentyl, 1-propionyloxypentyl, 1-butyryloxypentyl, 1-pivaloyloxypentyl or 1-pivaloyloxyhexyl group, 1-("cycloalkyl"carbonyloxy)-"lower alkyl groups" such as a cyclopentylcarbonyloxymethyl, cyclohexylcarbonyloxymethyl, 1-cyclopentylcarbonyloxyethyl, 1-cyclohexylcarbonyloxyethyl, 1-cyclopentylcarbonyloxypropyl, 1-cyclohexylcarbonyloxypropyl, 1-cyclopentylcarbonyloxybutyl or 1-cyclohexylcarbonyloxybutyl group, and 1-("aromatic acyl"oxy)-"lower alkyl groups" such as a benzoyloxymethyl group; (lower alkoxycarbonyloxy)alkyl groups such as a methoxycarbonyloxymethyl, ethoxycarbonyloxymethyl, propoxycarbonyloxymethyl, isopropoxycarbonyloxymethyl, butoxycarbonyloxymethyl, isobutoxycarbonyloxymethyl, pentyloxycarbonyloxymethyl, hexyloxycarbonyloxymethyl, cyclohexyloxycarbonyloxymethyl, cyclohexyloxycarbonyloxy(cyclohexyl)methyl, 1-(methoxycarbonyloxy)ethyl, 1-(ethoxycarbonyloxy)ethyl, 1-(propoxycarbonyloxy)ethyl, 1-(isopropoxycarbonyloxy)ethyl, 1-(butoxycarbonyloxy)ethyl, 1-(isobutoxycarbonyloxy) ethyl, 1-(t-butoxycarbonyloxy)ethyl, 1-(pentyloxycarbonyloxy)ethyl, 1-(hexyloxycarbonyloxy)ethyl, 1-(cyclopentyloxycarbonyloxy)ethyl, 1-(cyclopentyloxycarbonyloxy) propyl, 1-(cyclohexyloxycarbonyloxy)propyl, 1-(cyclopentyloxycarbonyloxy)butyl, 1-(cyclohexyloxycarbonyloxy)butyl, 1-(cyclohexyloxycarbonyloxy)ethyl, 1-(ethoxycarbonyloxy)propyl, 1-(methoxycarbonyloxy)propyl, 1-(ethoxycarbonyloxy)propyl, 1-(propoxycarbonyloxy) propyl, 1-(isopropoxycarbonyloxy)propyl, 1-(butoxycarbonyloxy)propyl, 1-(isobutoxycarbonyloxy)propyl, 1-(entyloxycarbonyloxy)propyl, 1-(hexyloxycarbonyloxy) propyl, 1-(methoxycarbonyloxy)butyl, 1-(ethoxycarbonyloxy)butyl, 1-(propoxycarbonyloxy)butyl, 1-(isopropoxycarbonyloxy)butyl, 1-(butoxycarbonyloxy)butyl, 1-(isobutoxycarbonyloxy)butyl, 1-(methoxycarbonyloxy) pentyl, 1-(ethoxycarbonyloxy)pentyl, 1-(methoxycarbonyloxy)hexyl or 1-(ethoxycarbonyloxy)hexyl group; oxodioxolenylmethyl groups such as a (5-phenyl-2-oxo-1, 3-dioxolen-4-yl)methyl, [5-(4-methylphenyl)-2-oxo-1,3-dioxolen-4-yl]methyl, [5-(4-methoxyphenyl)-2-oxo-1,3-dioxolen-4-yl]methyl, [5-(4-fluorophenyl)-2-oxo-1,3-dioxolen-4-yl]methyl, [5-(4-chlorophenyl)-2-oxo-1,3-dioxolen-4-yl]methyl, (2-oxo-1,3-dioxolen-4-yl)methyl, (5-methyl-2-oxo-1,3-dioxolen-4-yl)methyl, (5-ethyl-2-oxo-1,3-dioxolen-4-yl)methyl, (5-propyl-2-oxo-1,3-dioxolen-4-yl)methyl, (5-isopropyl-2-oxo-1,3-dioxolen-4-yl) methyl or (5-butyl-2-oxo-1,3-dioxolen-4-yl)methyl group; "phthalidyl groups" such as a phthalidyl, dimethylphthalidyl or dimethoxyphthalidyl group; the above-exemplified "lower aliphatic acyl groups"; the above-exemplified "aromatic acyl groups"; "half ester salt residues of succinic acid"; "phosphate ester salt residues"; "amino acids and the like residues capable of forming an ester"; a carbamoyl group; a carbamoyl group substituted by 1 or 2 lower alkyl groups; and "1-(acyloxy)alkyloxycarbonyl groups" such as a pivaloyloxymethyloxycarbonyl group, of which the "carbonyloxyalkyl groups" are preferred.

Preferred examples of the "protecting group removable in vivo by a biological method such as hydrolysis" related to the "ester formed with a carboxyl group" include "alkoxy (lower alkyl) groups", for example, (lower alkoxy)(lower alkyl) groups such as a methoxymethyl, 1-ethoxyethyl, 1-methyl-1-methoxyethyl, 1-(isopropoxy)ethyl, 2-methoxyethyl, 2-ethoxyethyl, 1,1-dimethyl-1-methoxymethyl, ethoxymethyl, n-propoxymethyl, isopropoxymethyl, n-butoxymethyl or t-butoxymethyl group, lower alkoxylated (lower alkoxy)(lower alkyl) groups such as a 2-methoxyethoxymethyl group, "aryl"oxy("lower alkyl groups") such as a phenoxymethyl group, and halogenated (lower alkoxy) (lower alkyl) groups such as a 2,2,2-trichloroethoxymethyl or bis(2-chloroethoxy)methyl group; ""lower alkoxy"carbonyl"lower alkyl groups"" such as a methoxycarbonylmethyl group; "cyano"lower alkyl groups"" such as a cyanomethyl or 2-cyanoethyl group; ""lower alkyl"thiomethyl groups" such as a methylthiomethyl or ethylthiomethyl group; ""aryl"thiomethyl groups" such as a phenylthiomethyl or naphthylthiomethyl group; ""lower alkyl"sulfonyl"lower alkyl groups" which may be substituted by halogen" such as a 2-methanesulfonylethyl or 2-trifluoromethanesulfonylethyl group; ""aryl"sulfonyl"lower alkyl groups"" such as a 2-benzenesulfonylethyl or 2-toluenesulfonylethyl group; the above-exemplified "1-(acyloxy)-"lower alkyl" groups"; the above-exemplified "phthalidyl groups"; aryl groups such as a phenyl or indanyl group; the above-exemplified "lower alkyl groups"; "carboxylalkyl groups" such as a carboxymethyl group; and "amino acids and the like residues capable of forming an amide" such as a phenylalanine group.

The term "other derivative" means a derivative of the above compound of formula (I) other than the above-described "ester" or the above-described "pharmacologically acceptable salt" which can be formed, if it has an amino and/or carboxyl group. Amide derivatives are such a derivative.

As for the prophylactic and therapeutic agent for glaucoma according to the present invention, angiotensin II antagonists as disclosed, for example, in EP795326, EP631780 (U.S. Pat. No. 5,250,521), WO95/21609 and WO91/15206 can be employed. These compounds can be prepared readily by a known process.

As for the "adrenaline receptor blocker", compounds as disclosed, for example, in GB1253710, GB1398455 and EP42299 can be employed. These compounds can be prepared readily by a known process.

As for the "prostaglandin" compounds as disclosed, for example, in EP289349 and WO90/02553 can be employed. These compounds can be prepared readily by a known process.

As for the "carbonic anhydrase inhibitor", compounds as disclosed, for example, in EP296879 can be employed and they can be prepared readily by a known process.

The entire contents of each of the following above described publications are hereby incorporated by reference herein: EP795326, EP631780, U.S. Pat. No. 5,250,521, WO95/21609, WO91/15206, GB1253710, GB1398455, EP42299, EP289349, WO90/02553 and EP296879.

In the prophylactic and therapeutic agent for glaucoma according to the present invention, a pharmaceutical composition for simultaneous use of the angiotensin II antagonist and at least one compound selected from the adrenaline receptor blockers, prostaglandins and carbonic anhydrase inhibitors can be prepared in a manner known per se in the art by using compounds serving as active ingredients (more specifically, an angiotensin II antagonist and at least one compound selected from the adrenaline receptor blockers, prostaglandins and carbonic anhydrase inhibitors). This pharmaceutical composition is preferably prepared in a form suited for topical application to the eyes, for example, eye drops such as aqueous ophthalmic solutions, aqueous ophthalmic suspensions, non-aqueous ophthalmic solutions and non-aqueous ophthalmic suspensions, gels, and ophthalmic ointments. Upon formulation, a pharmacologically acceptable carrier can be used. No particular limitation is imposed on the carrier usable here insofar as it is ordinarily employed for the preparation of ophthalmic formulations. Examples of the carriers include inert diluents, preservatives, isotonic agents, buffers, stabilizers, pH regulators, thickeners, surfactants and ointment bases.

Examples of the inert diluent include aqueous solvents such as water, Ringer's solution and isotonic saline solution and oil solvents such as castor oil, olive oil, sesame oil, soybean oil, liquid paraffin, propylene glycol and β-octyldodecanol.

Examples of the preservative include parabens such as methylparaben, ethylparaben, propylparaben and butylparaben, benzalkonium chloride, chlorhexidine, benzethonium chloride, benzyl alcohol, sorbic acid and salt thereof, thimerosal and chlorobutanol, of which the parabens, benzalkonium chloride and benzethonium chloride are preferred.

Examples of the isotonic agent include sodium chloride, mannitol, sorbitol and glycerin.

Examples of the buffer include boric acid, borates, phosphates, acetates and citrates.

Examples of the stabilizer include ethylenediamine tetraacetate.

Examples of the pH regulator include hydrochloric acid, acetic acid and sodium hydroxide.

Examples of the ointment base include vaseline, plastibase and liquid paraffin.

Examples of the thickener include methyl cellulose, carmellose and salts thereof, hydroxyethyl cellulose, sodium alginate, carboxyvinyl polymer and polyvinylpyrrolidone.

Examples of the surfactant include polyethylene glycol, propylene glycol, polyoxyethylene hydrogenated castor oil and Polysorbate.

For the preparation of a gel, carboxyvinyl polymer, methyl cellulose, sodium alginate, hydroxypropyl cellulose or ethylene maleic anhydride polymer are usable.

The above-described pharmaceutical composition can contain compounds serving as active ingredients at a concentration ranging from the lower limit of 0.001 volume % (preferably 0.01 volume %) to the upper limit of 10 volume % (preferably 5 volume %). The "concentration" refers to one of the active ingredients, that is, it could be (i) the concentration of the angiotensin II in the present composition or it could be the concentration of (ii) the at least one compound selected from the group consisting of an adrenaline receptor blocker, a prostaglandin and a carbonic inhibitor. The "concentration" does not refer to both active ingredients.

Ratios of the active ingredients, i.e., ratios of (i) the angiotensin II antagonist to (ii) the at least one compound selected from the group consisting of an adrenaline receptor blocker, a prostaglandin and a carbonic anhydrase inhibitor, are as follows:

when (ii) is an adrenaline receptor blocker, the ratio (i):(ii) is from 10:1 to 100:1;

when (ii) is a prostaglandin, the ratio (i):(ii) is from 100:1 to 1000:1;

when (ii) is a carbonic inhibitor, the ratio (i):(ii) is from 1:1 to 10:1.

Although the dose of the pharmaceutical composition varies depending on the symptom or the like, it can be administered by one to several drops, preferably 1 to 2 drops (one drop amounts to about 50 μL) at a time, once or in about 6 times a day.

The above-described pharmaceutical composition can also be prepared, for example, in the form suitable for oral administration such as tablets, capsules, granules, powders or syrups or for parenteral administration such as injection or suppository. These formulations can be prepared by well known methods using additives such as excipients (examples include organic excipients, e.g., sugar derivatives such as lactose, sucrose, glucose, mannitol and sorbitol, starch derivatives such as corn starch, potato starch, α-starch, dextrin and carboxymethyl starch, cellulose derivatives such as crystalline cellulose, low substituted hydroxypropyl cellulose, hydroxypropylmethyl cellulose, carboxymethyl cellulose, calcium carboxymethyl cellulose and sodium internally-cross-linked carboxymethyl cellulose, acacia, dextran, and Pullulan; and inorganic excipients, e.g., silicate derivatives such as light silicic anhydride, synthetic aluminum silicate and magnesium metasilicate aluminate, phosphates such as calcium phosphate, carbonates such as calcium carbonate, and sulfates such as calcium sulfate); lubricants (examples include stearic acid, metal stearates such as calcium stearate and magnesium stearate, talc, colloidal silica, waxes such as beeswax and spermaceti, boric acid, adipic acid, sulfates such as sodium sulfate, glycol, fumaric acid, sodium benzoate, DL-leucine, sodium salts of fatty acids, lauryl sulfates such as sodium lauryl sulfate and magnesium lauryl sulfate; silicic acids such as silicic anhydride and silicic acid hydrate, and the above-exemplified starch derivatives); binders (examples include polyvinylpyrrolidone, macrogol, and similar compounds to the excipients exemplified above); disintegrators (examples include similar compounds to the excipients exemplified above, and chemically modified starches and celluloses such as sodium crosscarmellose, sodium carboxymethylstarch and cross-linked polyvinylpyrrolidone); stabilizers (examples include paraoxybenzoates such as methylparaben and propylparaben, alcohols such as chlorobutanol, benzyl alcohol and phenylethyl alcohol, benzalkonium chloride, phenol derivatives such as phenol and cresol, thimerosal, dehydroacetic acid, and sorbic acid), corrigents (examples include sweeteners, souring agents and flavors which are usually used) and diluents.

The amount of the pharmaceutical composition varies, depending upon the symptom and age of the patient (warm blooded animal, such as a human) and the administration route. It is, however, desirable to orally administer the active ingredients in an amount ranging from 0.01 mg/kg body weight (preferably 0.1 mg/kg body) as a lower limit to 100 mg/kg body weight (preferably 50 mg/kg body weight) as an upper limit once. While it is desirable to intravenously administer it in an amount ranging from 0.01 mg/kg body weight (preferably 0.05 mg/kg body weight) as a lower limit to 100 mg/kg body weight (preferably 50 mg/kg body weight) as an upper limit once. In either case, the active ingredients are preferably administered once to several times a day.

In the prophylactic and therapeutic agent for glaucoma according to the present invention, a pharmaceutical composition for separate or successive use of the angiotensin II antagonist and at least one compound selected from the adrenaline receptor blockers, prostaglandins and carbonic anhydrase inhibitors can be prepared by individually formulating the compounds serving as active ingredients (that is, angiotensin II antagonist and at least one compound selected from the adrenaline receptor blockers, prostaglandins and carbonic anhydrase inhibitors). The formulation can be carried out in accordance with the above-described methods. At this time, these formulations may be in the same form or a different form. Forms suitable for topical application to the eyes are especially preferred.

The present invention will hereinafter be described in further detail by Examples. It should however be borne in mind that the present invention is not limited to or by them.

EXAMPLES

Example 1

Using New Zealand White Rabbits having body weights of 2 to 3 kg, ocular hypertension models were prepared in accordance with the method of Kurihara, et al. (Jpn. J. Ocular Pharmacology, 4, 62-64(1990)) and the intraocular pressure lowering action of the test compounds was investigated.

Described specifically, the rabbits were maintained under general anesthesia and their intraocular pressure was measured using a tonometer ("Alcon Applanation Pneumatonography"; manufactured by Alcon). After instillation of local anesthetics into the eyes of the rabbits, 0.1 ml of a 5% sodium chloride solution were injected into their vitreous bodies through a 30 gauge needle. An increase in the intraocular pressure was confirmed 30 minutes after injection, followed by administration of 50 μl of an eye drop solution containing the test compound. Their intraocular pressure was then measured for 2 hours at intervals of 30 minutes (single administration test).

In the combined administration test, after confirmation of an increase in the intraocular pressure, 50 μl of the solution of the first test compound was administered, followed by the administration of the same amount of the solution of the second test compound after 5 minutes. After the second administration, the intraocular pressure was measured for 2 hours at intervals of 30 minutes.

The below-described compound A was dissolved in a suitable amount of an sodium hydroxide solution and this solution was used as a test compound. With regards to the below-described compounds B to E, commercially available eye drops were employed as the test compound.

Compound A:

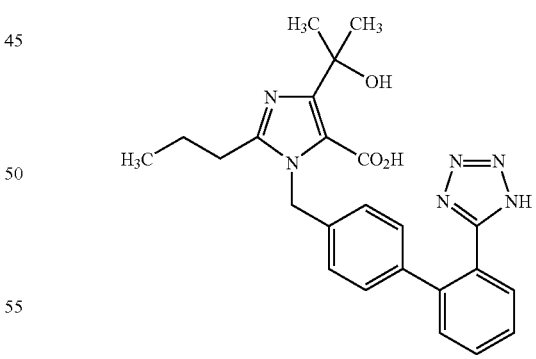

Compound B: timolol maleate
Compound C: isopropyl unoprostone
Compound D: latanoprost
Compound E: dorzolamide hydrochloride When Compound A which is an angiotensin II antagonist was administered in combination with any one of Compounds B, C, D and E, intraocular pressure lowering action was potentiated.

Example 2

Intraocular Pressure Lowering Action (2)

Using a tonometer ("Alcon Applanation Pneumatonography; manufactured by Alcon), the intraocular pressure of each of New Zealand White Rabbits having body weights of 2 to 3 kg was measured (without anesthesia), followed by administration of 50 µl of a test compound in the form of eye drops. The intraocular pressure was then measured for 4 hours at intervals of one hour (single administration test).

In the combined administration test, after measurement of the intraocular pressure, 50 µl of the first test compound solution was administered, followed by the administration of the same amount of the second test compound solution after 5 minutes. After the second administration, the intraocular pressure was measured for 4 hours at intervals of 1 hour.

Also in this Example, the same test compounds as described in Example 1 were employed.

When Compound A which is an angiotensin II antagonist was administered in combination with any one of Compounds B, C, D and E, intraocular pressure lowering action was potentiated.

Example 3

Intraocular Pressure Lowering Test (3)

After the measurement of the intraocular pressure as in Example 2, 50 µl of a solution of test compound 1 was instilled into the eyes, followed by administration of the same amount of the solution of test compound 2 after 5 minutes. Four hours after the second administration, the intraocular pressure was measured and the change ratio of the intraocular pressure was determined by the below-described equation:

The change ratio of intraocular pressure (%)=[(intraocular pressure after administration of eye drops−intraocular pressure before administration of eye drops)/intraocular pressure before administration of eye drops]×100.

In this Example, the same test compounds as Example 1 were employed. The results are shown below in Tables 1 and 2.

TABLE 1

Combined administration of Compound A and Compound C

| Test compound 1 | Test compound 2 | Change ratio (%) of intraocular pressure |
|---|---|---|
| Physiological saline | Physiological saline | 7.3 ± 3.7 |
| Compound A (4%) | Physiological saline | 11.4 ± 5.5 |
| Physiological saline | Compound C (0.12%) | −2.4 ± 9.1 |
| Compound A (4%) | Compound C (0.12%) | −15.3 ± 4.5 |

TABLE 2

Combined administration of compound A and Compound D

| Test compound 1 | Test compound 2 | Change ratio (%) of intraocular pressure |
|---|---|---|
| Physiological saline | Physiological saline | 1.7 ± 4.4 |
| Compound A (4%) | Physiological saline | 11.5 ± 4.1 |
| Physiological saline | Compound D (0.005%) | 17.2 ± 8.8 |
| Compound A (4%) | Compound D (0.005%) | −8.2 ± 4.7 |

As is apparent from the Tables 1 and 2, synergistic intraocular pressure lowering action was observed when the angiotensin II antagonist (Compound A) and the prostaglandin (Compound C or D) were administered in combination.

Example 4

Intraocular Pressure Lowering Test (4)

An ocular hypertension model was made as in Example 1. After confirmation of an increase in the intraocular pressure, 50 µl of a test compound 1 was instilled to the eyes, followed by application of the same amount of a test compound 2 into the eyes after 5 minutes. After this second administration, the intraocular pressure was measured for 2 hours at intervals of 1 hour. Intraocular pressure lowering was determined by the below-described equation.

Decrease in intraocular pressure (mmHg)=(intraocular pressure after instillation of a compound group−intraocular pressure before instillation of the compound group)−(intraocular pressure after instillation of a control group−intraocular pressure before instillation of the control group)

The term "control group" in the above-described formula means a group to which physiological saline was administered to the eyes instead of each of the test compound 1 and test compound 2. Groups other than this control group are a compound group.

Also in this Example, the same test compounds as described in Example 1 were employed. The results are shown below in Table 3.

TABLE 3

Combined administration of Compound A with Compound B

| Test Compound 1 | Test Compound 2 | Decrease in intraocular pressure (mmHg) Time after instillation (min) | | |
|---|---|---|---|---|
| | | 0 | 60 | 120 |
| Physiological saline | Physiological saline | 0 | 0 | 0 |
| Compound A (1%) | Physiological saline | 0.0 ± 2.1 | −1.7 ± 2.2 | −3.4 ± 1.7 |
| Physiological saline | Compound B (0.25%) | 0.0 ± 1.5 | −2.0 ± 3.5 | −1.9 ± 3.2 |
| Compound A (1%) | Compound B (0.25%) | 0.0 ± 0.9 | −5.0 ± 2.4 | −7.4 ± 1.8 |

As is apparent from Table 3, stronger intraocular pressure lowering action was observed when the angiotensin II antagonist (Compound A) was administered in combination with timolol maleate (Compound B).

FORMULATION EXAMPLES

Formulation Example 1

An Eye Drop Containing Compound A and Timolol Maleate

| | |
|---|---|
| Compound A | 0.001 g |
| Timolol maleate | 0.001 g |
| Disodium phosphate | 0.716 g |
| Monosodium phosphate | 0.728 g |
| Sodium chloride | 0.400 g |
| Methyl p-hydroxybenzoate | 0.026 g |
| Propyl p-hydroxybenzoate | 0.014 g |
| Sterilized purified water | q.s. |
| Sodium hydroxide | q.s. |
| Total amount | 100 ml |

Formulation Example 2

Combination of an Eye Drop of Compound A and an Eye Drop of Isopropyl Unoprostone

| | |
|---|---|
| Compound A | 0.002 g |
| Disodium phosphate | 0.716 g |
| Monosodium phosphate | 0.728 g |
| Sodium chloride | 0.400 g |
| Methyl p-hydroxybenzoate | 0.026 g |
| Propyl p-hydroxybenzoate | 0.014 g |
| Sterilized purified water | q.s. |
| Sodium hydroxide | q.s. |
| Total amount | 100 ml |

| | |
|---|---|
| Isopropyl unoprostone | 0.002 g |
| Disodium phosphate | 0.716 g |
| Monosodium phosphate | 0.728 g |
| Sodium chloride | 0.400 g |
| Methyl p-hydroxybenzoate | 0.026 g |
| Propyl p-hydroxybenzoate | 0.014 g |
| Sterilized purified water | q.s. |
| Sodium hydroxide | q.s. |
| Total amount | 100 ml |

Formulation Example 3

Combination of an Eye Drop of Compound A and an Eye Drop of Latanoprost

| | |
|---|---|
| Compound A | 0.002 g |
| Disodium phosphate | 0.716 g |
| Monosodium phosphate | 0.728 g |
| Sodium chloride | 0.400 g |
| Methyl p-hydroxybenzoate | 0.026 g |
| Propyl p-hydroxybenzoate | 0.014 g |
| Sterilized purified water | q.s. |
| Sodium hydroxide | q.s. |
| Total amount | 100 ml |

| | |
|---|---|
| Latanoprost | 0.002 g |
| Disodium phosphate | 0.716 g |
| Monosodium phosphate | 0.728 g |
| Sodium chloride | 0.400 g |
| Methyl p-hydroxybenzoate | 0.026 g |
| Propyl p-hydroxybenzoate | 0.014 g |
| Sterilized purified water | q.s. |
| Sodium hydroxide | q.s. |
| Total amount | 100 ml |

Administration of an angiotensin II antagonist in combination with at least one compound selected from an adrenaline receptor blocker, a prostaglandin and a carbonic anhydrase inhibitor makes it possible to attain an excellent intraocular pressure lowering effect. The pharmaceutical composition of the present invention is therefore useful as a prophylactic or therapeutic agent for glaucoma.

What is claimed is:

1. A pharmaceutical composition for topical administration to an eye for treating glaucoma comprising a pharmaceutically effective amount of a combination of (i) an angiotensin II antagonist, wherein said angiotensin II antagonist is a compound of the following formula (I) or a pharmacologically acceptable salt or ester thereof:

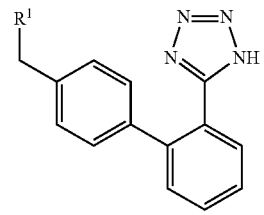

wherein $R^1$ represents the following structural formula

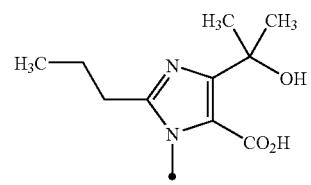

and (ii) a prostaglandin which is isopropyl unoprostone, and optionally (iii) a pharmaceutically acceptable carrier,
wherein the angiotensin II antagonist and the prostaglandin are present in sufficient amounts to form a synergistically effective composition for lowering intraocular pressure,
wherein a ratio of the amounts of the angiotensin II antagonist to the isopropyl unoprostone is 33:1.

2. A pharmaceutical composition for topical administration to an eye for treating glaucoma comprising a pharmaceutically effective amount of a combination of (i) an angiotensin II antagonist, wherein said angiotensin II antagonist is a compound of the following formula (I) or a pharmacologically acceptable salt or ester thereof:

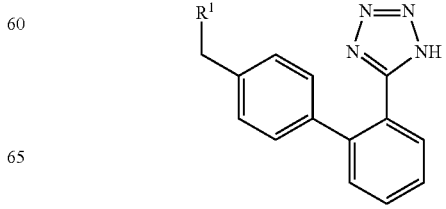

wherein R¹ represents the following structural formula

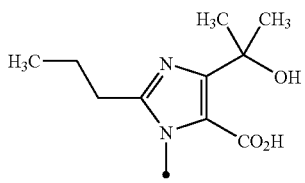
(Ia)

(ii) a prostaglandin which is latanoprost,
and optionally (iii) a pharmaceutically acceptable carrier,
wherein the angiotensin II antagonist and the prostaglandin are present in sufficient amounts to form a synergistically effective composition for lowering intraocular pressure,
wherein a ratio of the amounts of the angiotensin II antagonist to the latanoprost is 800:1.

3. A method for treating glaucoma and reducing intraocular pressure comprising topically administering to an eye of a human in need thereof a pharmaceutically effective amount of the pharmaceutical composition according to claim 1.

4. A method for treating glaucoma and reducing intraocular pressure comprising topically administering to an eye of a human in need thereof a pharmaceutically effective amount of the pharmaceutical composition according to claim 2.

* * * * *

UNITED STATES PATENT AND TRADEMARK OFFICE
CERTIFICATE OF CORRECTION

PATENT NO. : 7,307,096 B2 Page 1 of 1
APPLICATION NO. : 10/146747
DATED : December 11, 2007
INVENTOR(S) : Tomihisa Yokoyama It is certified that error appears in the above-identified patent and that said Letters Patent is hereby corrected as shown below:

On the Title page,

[*] Notice: Subject to any disclaimer, the term of this patent is extended or adjusted under 35 USC 154(b) by (732) days Delete the phrase "by 732 days" and insert -- by 752 days --

Signed and Sealed this

Nineteenth Day of August, 2008

JON W. DUDAS
*Director of the United States Patent and Trademark Office*